US009127018B2

(12) United States Patent
Ciceri et al.

(10) Patent No.: US 9,127,018 B2
(45) Date of Patent: Sep. 8, 2015

(54) SOLID FORMS OF ORTATAXEL

(71) Applicant: Indena S.p.A., Milan (IT)

(72) Inventors: Daniele Ciceri, Milan (IT); Nicola Sardone, Milan (IT); Bruno Gabetta, Milan (IT); Maurizio Ricotti, Milan (IT)

(73) Assignee: Indena S.p.A., Milan (IT)

( * ) Notice: Subject to any disclaimer, the term of this patent is extended or adjusted under 35 U.S.C. 154(b) by 0 days.

(21) Appl. No.: 14/102,365

(22) Filed: Dec. 10, 2013

(65) Prior Publication Data

US 2014/0128459 A1  May 8, 2014

Related U.S. Application Data

(63) Continuation of application No. 12/863,167, filed as application No. PCT/EP2009/000112 on Jan. 12, 2009, now abandoned.

(30) Foreign Application Priority Data

Jan. 18, 2008 (EP) .................................... 08000904

(51) Int. Cl.
  *C07D 305/06* (2006.01)
  *C07D 305/14* (2006.01)
  *C07D 493/06* (2006.01)
  *C07D 493/08* (2006.01)

(52) U.S. Cl.
  CPC ............ *C07D 493/06* (2013.01); *C07D 305/06* (2013.01); *C07D 305/14* (2013.01); *C07D 493/08* (2013.01)

(58) Field of Classification Search
  CPC ............................ C07D 305/06; C07D 305/14
  USPC .................................................. 549/510, 511
  See application file for complete search history.

(56) References Cited

U.S. PATENT DOCUMENTS

| | | | |
|---|---|---|---|
| 5,319,112 A | 6/1994 | Kingston et al. | |
| 5,367,086 A | 11/1994 | Rao | |
| 5,475,011 A | 12/1995 | Ojima et al. | |
| 5,476,954 A | 12/1995 | Bourzat et al. | |
| 5,599,820 A | 2/1997 | Ojima et al. | |
| 5,621,121 A | 4/1997 | Commercon et al. | |
| 5,698,712 A | 12/1997 | Bombardelli et al. | |
| 5,705,508 A | 1/1998 | Ojima et al. | |
| 5,750,562 A | 5/1998 | Bombardelli et al. | |
| 5,763,628 A | 6/1998 | Bourzat et al. | |
| 5,917,056 A | 6/1999 | Bombardelli et al. | |
| 5,973,163 A | 10/1999 | Bombardelli et al. | |
| 6,022,985 A | 2/2000 | Authelin et al. | |
| 6,737,534 B2 * | 5/2004 | Pontiroli et al. ............... | 549/296 |
| 6,906,101 B1 * | 6/2005 | Bombardelli et al. ......... | 514/463 |
| 7,078,432 B2 | 7/2006 | Bombardelli et al. | |
| 7,232,916 B1 * | 6/2007 | Gabetta et al. ................. | 549/296 |
| 7,317,113 B2 | 1/2008 | Bombardelli et al. | |
| RE40,901 E | 9/2009 | Bombardelli et al. | |
| 2006/0116420 A1 | 6/2006 | Chidambaram et al. | |
| 2007/0212394 A1 | 9/2007 | Reyes et al. | |
| 2011/0054015 A1 | 3/2011 | Ciceri | |

FOREIGN PATENT DOCUMENTS

| | | |
|---|---|---|
| EP | 604910 | 7/1994 |
| EP | 629701 | 12/1994 |
| EP | 559019 | 9/1999 |
| EP | 1307436 | 9/2004 |
| EP | 1947094 | 7/2008 |
| WO | 91/07842 | 5/1991 |
| WO | 92/07842 | 5/1992 |
| WO | 92/09589 | 6/1992 |
| WO | 94/07879 | 4/1994 |
| WO | 94/13655 | 6/1994 |
| WO | 94/22856 | 10/1994 |
| WO | 94/27984 | 12/1994 |
| WO | 94/29288 | 12/1994 |
| WO | 96/29321 | 9/1996 |
| WO | 96/30373 | 10/1996 |
| WO | 96/36622 | 11/1996 |
| WO | 97/43291 | 11/1997 |
| WO | 98/30553 | 7/1998 |
| WO | 01/02407 | 1/2001 |
| WO | 02/12215 | 2/2002 |
| WO | 02/44161 | 6/2002 |

(Continued)

OTHER PUBLICATIONS

Appendino et al., "A New Rearrangement of Oxetane-Type Taxoids." Tetrahedron Lett. 1994, vol. 35, p. 2217-2220.
Appendino et al., "The Synthesis of A-Nor-B-homobaccatin III Derivatives." Tetrahedron Letters (1994), vol. 35, No. 35, pp. 6547-6550.
Appendino et al., Synthesis and Evaluation of C-seco-paclitaxel analogues. Tetrahedron Letters, vol. 38, No. 24, pp. 4273-4276 (1997).
Baldelli et al., Diastereoselective 14beta-hydroxylation of baccatin III derivatives. J. Org. Chem., 68, 9773-9779 (2003).

(Continued)

*Primary Examiner* — Noble Jarrell
*Assistant Examiner* — Raymond Covington
(74) *Attorney, Agent, or Firm* — K&L Gates LLP; Louis C. Cullman; Hal Gibson (57) ABSTRACT

The present invention relates to solid forms of 13-(N-Boc-β-isobutylserinyl)-14-β hydroxybaccatin III 1, 14-carbonate (Ortataxel). Amorphous Form A, crystalline Form B, mixtures thereof and processes for preparing them are disclosed. Amorphous Form A is prepared by fast precipitation of Ortataxel from a mixture of acetone and water. Form A transforms in Form B when suspended and stirred in a mixture of ethanol and water for 4-8 hours. If the suspension is stirred for less than 4 hours, mixtures of Form B and Form A are obtained. Form B or mixtures of Forms A and B can also be obtained dissolving Ortataxel in a protic organic solvent, followed by addition of water.

27 Claims, 13 Drawing Sheets

(56) References Cited

FOREIGN PATENT DOCUMENTS

| WO | 03/035633 | 5/2003 |
|----|-----------|--------|
| WO | 2007/078050 | 7/2007 |
| WO | 2007/131601 | 11/2007 |
| WO | 2009/090024 | 7/2009 |

OTHER PUBLICATIONS

Hennenfent et al., "Novel Formulations of Taxanes: A Review. Old Wine in a Bew Bottle?" Annals of Oncology, vol. 17, No. 5, 2006, p. 735-749.

Holton et al., Selective protection of the C(7) and C(10) hydroxyl groups in 10-deacetyl baccatin II. Tetrahedron Letters, pp. 2883-2886 (1998).

Kant et al., Synthesis and antitumor properties of novel 14-b-hydroxytaxol and related analogues. Bioorganic & Medicinal Chemistry Letters, vol. 4, No. 13, pp. 1565-1570 (1994).

Nicoletti et al., "IDN5109, a taxane with oral bioavailability and potent antitumor activity," Cancer Research, vol. 60, No. 4, 2000, p. 842-846.

Ojima et al., "Structure-Activity Relationships of New Taxoids Derived from 14b-Hydroxy-10-deacetylbaccatin III." J. Med. Chem. (1994), 37, 1408-1410.

Ojima et al., "Synthesis and Biological Activity of 14-Hydroxydocetaxel." Bioorganic & Medicinal Chemistry Letters (1994), vol. 4, No. 13, pp. 1571-1576.

Ojima et al., Syntheses and Structure—Activity Relationships of Taxoids Derived from 14beta-hydroxy-10-deacetylbaccatin III. J. Med. Chem., 40, 267-278 (1997).

Ringel et al., Taxol is converted to 7-epitaxol, a biologically active isomer, in cell culture medium. The Journal of Pharmacology and Experimental Therapeutics, vol. 242, No. 2, pp. 692-698 (1987).

Bayes et al., Gateways to Clinical Trials. Methods Find Exp. Clin. Pharmacol., 26, (1):53-84 (2004).

Bayes et al., Gateways to Clinical Trials. Methods Find Exp. Clin. Pharmacol., 26, (3):211-244 (2004).

Bayes et al., Gateways to Clinical Trials. Methods Find Exp. Clin. Pharmacol., 26, 639 (2004).

Caira, Crystalline Polymorphism of Organic Compounds, Topics in Current Chemisty, vol. 198, pp. 163-208 (1998).

Cui, Historical Perspectives: A material science perspective of pharmaceutical solids. International Journal of Pharmaceutics 339, 3-18 (2007).

Drugs of the Future, 2001, 26 (6), p. 533-544.

Geney et al., Recent advances in the new generation taxane anticancer agents. Medicinal Chemisty, (1):125-139 (2005).

International Search Report for PCT/EP2009/000112 filed on Jan. 12, 2009.

Shah et al., Review: Analytical techniques for quantification of amorphous/crystalline phases in pharmaceutical solids. Journal of Pharmaceutical Sciences, vol. 95, No. 8, pp. 1641-1665 (2006).

Takeuchi et al., A comparative study on the neurotoxcitiy of n-pentane, n-hexane, and n-heptane in the rat. British Journal of Industrial Medicine, vol. 37, No. 3, pp. 241-247 (1980).

Tomillero et al., Gateways to Clinical Trials. Methods Find Exp. Clin. Pharmacol., 30(8):643-672 (2008).

* cited by examiner

Fig. 2 - DSC profile of Form A

Fig. 10 - DSC profile of Mixture of Form A and Form B

Fig.12 - TG/DT profile of Mixture of Form A and Form B

SOLID FORMS OF ORTATAXEL

CROSS-REFERENCE TO RELATED APPLICATIONS

This application is a continuation of U.S. patent application Ser. No. 12/863,167 filed on Nov. 18, 2010 which is a 371 application of international application number PCT/EP2009/000112 filed on Jan. 12, 2009, which claims priority to EP 08000904.6, filed Jan. 18, 2008; the disclosures each of which are incorporated herein by reference in their entirety.

FIELD OF THE INVENTION

The present invention relates to solid forms of Ortataxel (13-(N-Boc-β-isobutylserinyl)-14-β-hydroxybaccatin III 1,14-carbonate) (1), mixtures thereof and methods for their preparation.

(1)

BACKGROUND OF THE INVENTION

Ortataxel (1) is an antitumor compound particularly active against breast, lung, ovary, colon, prostate, kidney and pancreas tumors, even in case of resistance to known antitumor agents such as adriamycin, vinblastine and some platinum derivatives.

(1)

Ortataxel can be prepared according to the methods described in U.S. Pat. No. 7,232,916, in U.S. Pat. No. 6,737,534 and in U.S. Pat. No. 6,906,101. These patents disclose in the examples a final purification step consisting of crystallization from a mixture of acetone and hexane, which gives Ortataxel in the form of a solvate with an acetone content ranging from 4.5 to 6.5%.

The XRPD of the acetone solvate shows distinctive peaks at approximately 7.9, 9.8, 10.6, 10.9, 14.6, 16.9, 19.7, 21.3 deg 2-theta. The DSC curve shows an endothermic peak with onset at about 164° C. due to melting and release of the crystallization solvent (confirmed by a weight loss of about 5.0% in TG/DTA) and a weak exothermic peak with maximum at about 212° C. followed by an intense endothermic peak with maximum at about 247° C. due to melting and incipient decomposition. The IR shows characteristic absorption frequencies at 3521, 3321, 2971, 2953, 1826, 1762, 1706, 1526, 1366, 1238, 1165, 1072, 723 cm$^{-1}$.

It is well known that volatile impurities in active pharmaceutical ingredients must comply with ICH (International Conference on Harmonisation) guidelines (Q3C); in this specific case an acetone content from 4.5 to 6.5% would not be allowed. Thus, it would be desirable to find a stable crystalline form of Ortataxel which does not contain residual solvents in amounts unacceptable from a regulatory point of view. Such crystalline form should also be chemically and thermodynamically stable, i.e. it should keep the same quality during storage, and should be obtainable through a reproducible method.

DISCLOSURE OF THE INVENTION

It has now been found that Ortataxel exists in two non-solvated physical Forms, herein after referred to as Forms A and B, which can also be obtained as mixtures.

Form A is an amorphous solid, since it shows an X-ray powder diffraction pattern with no discernable peaks. It can be easily prepared from Ortataxel, for example Ortataxel acetone solvate obtained according to the synthetic procedures described in the above-cited patents, by dissolution in a suitable water-miscible solvent, followed by fast addition of water containing traces (usually 0.001-0.003% w/v) of an organic acid such as acetic or ascorbic acid, preferably citric. "Suitable water-miscible solvent" means a ketone or an aprotic dipolar solvent or a mixture thereof; preferred solvents are acetone, dimethylsulfoxide and mixtures thereof. The process is usually carried out at a temperature ranging from 20 to 30° C.; and the preferred organic acid is citric acid. The organic acid avoids undesired formation of the 7-epimer and makes Form A physically and chemically stable for at least 36 months. According to a preferred embodiment, the preparation of Form A is carried out dissolving Ortataxel in acetone (8 mL/$g_{ortataxel}$) and precipitating it with a water (40 mL/$g_{ortataxel}$) containing 0.001-0.003% w/v citric acid, at room temperature.

Form B is a crystalline polymorph melting at 159° C.; with respect to the pseudopolymorhic acetone solvate, Form B is characterized by a low solvent content, ease of isolation by filtration or centrifugation and chemical and physical stability for at least 36 months. Form B can be prepared dissolving Ortataxel, for example the acetone solvate or the above form A, in a protic organic solvent, such as methanol, ethanol or isopropanol, preferably ethanol, containing traces of an organic acid (0.01-0.03% w/v), such as acetic, ascorbic but preferably citric acid, followed by addition of water until precipitation and stirring the resulting mixture at a temperature ranging from 0 to 60° C., preferably at 40° C., for a time ranging from 4 to 8 hours. According to a preferred embodiment, the preparation of Form B is carried out dissolving Ortataxel in ethanol (8-12 mL/$g_{ortataxel}$) containing 0.01-0.03% w/v of citric acid, followed by addition of water (13-20 mL/$g_{ortataxel}$), so that the ethanol/water ratio ranges between 0.5-0.7, and stirring for 6 hours. If stirring is carried out for less than 4 hours, Ortataxel is obtained as a mixture of Form A and Form.

Ortataxel Forms A and B and mixtures thereof can advantageously be used for the preparation of pharmaceutical compositions for the treatment of cancer. In particular, mixtures of form A and B, which•have different bioavailabilities, are useful for the preparation of controlled-release solid Forms. Therefore, a further object of the present invention are pharmaceutical compositions containing Ortataxel crystalline Form A or B or mixtures thereof in admixture with pharmaceutically acceptable carriers and/or ingredients; for example those disclosed in "Remington's Pharmaceutical Sciences", Mack Publishing Co., N.Y., USA. The invention is now illustrated in greater detail in the following experimental section.

EXPERIMENTAL SECTION

Description of the Figures

X-ray powder diffraction (XRPD), differential scanning calorimetry (DSC), thermogravimetric/differential thermal analyses (TG/DTA), infrared (IR), and optical microscopy were used to characterize the new solid Forms which are compared with the analytical data of the acetone solvate.

FORM A

Figure 1:
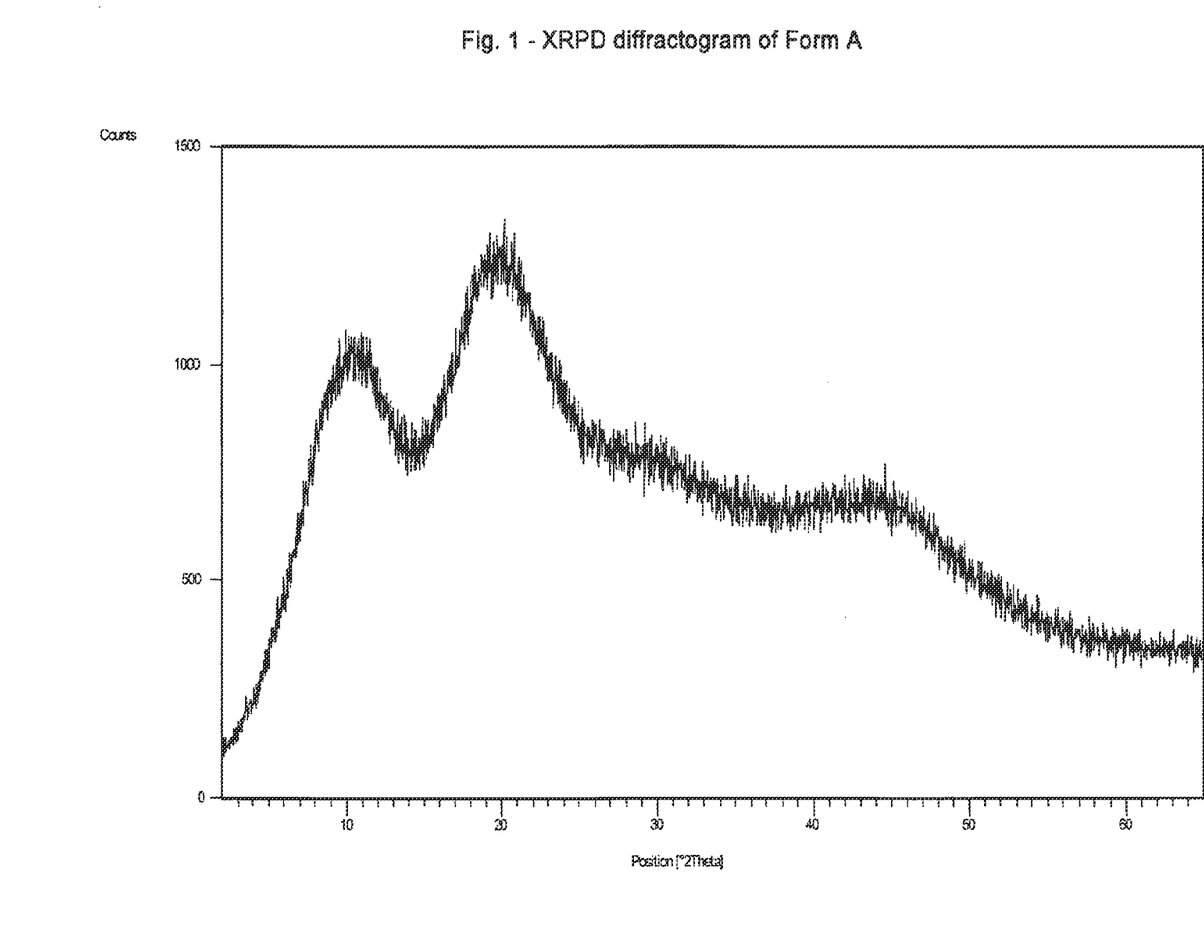
FIGS. 1-4: XRPD, DSC,TG/DTA and IR spectra of Form A.

The x-ray powder diffraction pattern of Form A (FIG. 1) is typical for an amorphous product with complete absence of diffraction peaks.

Figure 2:
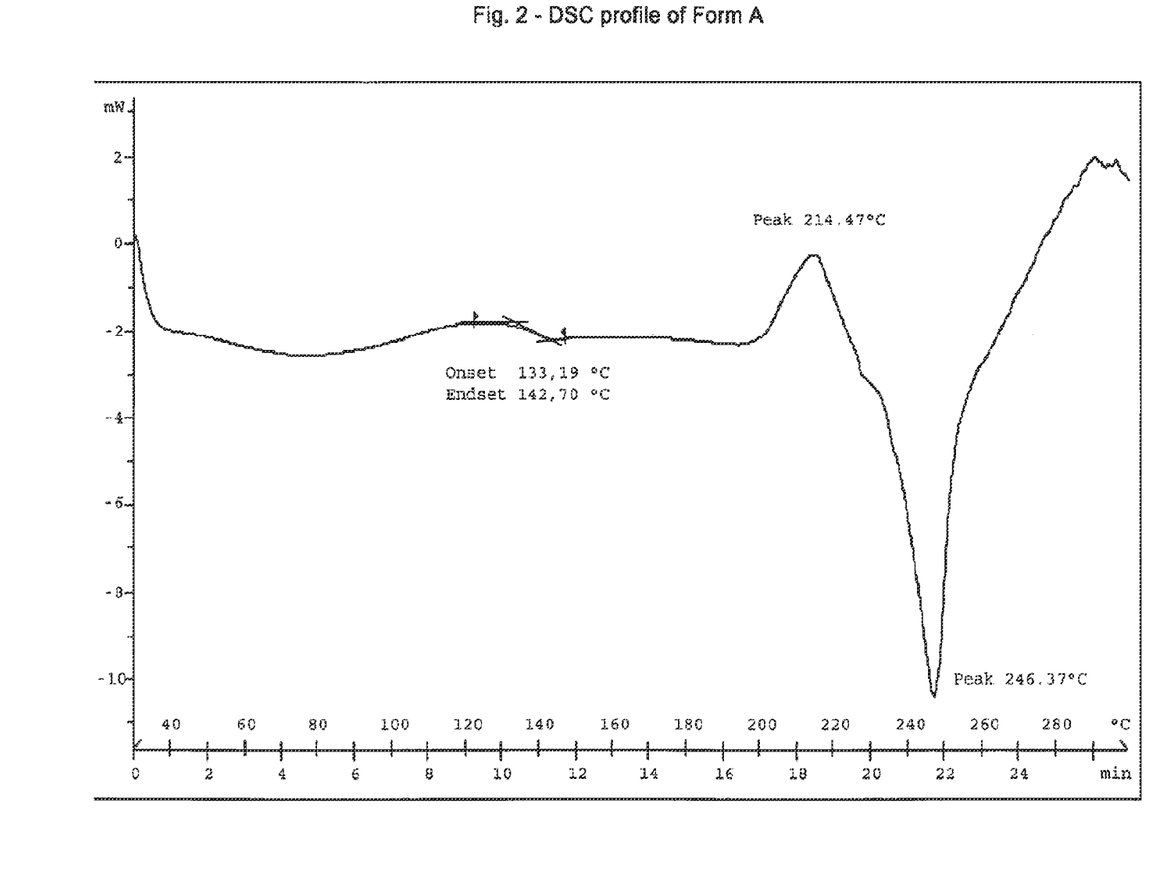

The DSC curve of Form A (FIG. 2) shows a weak and broad endothermic signal with maximum at about 80° C., a baseline deflection due to $T_g$ between 133° C. and 143° C., an exothermic peak with maximum at about 214° C. due to recrystallisation of the melted product and the consequent melting peak with maximum at about 246° C. followed by decomposition.

Figure 3:
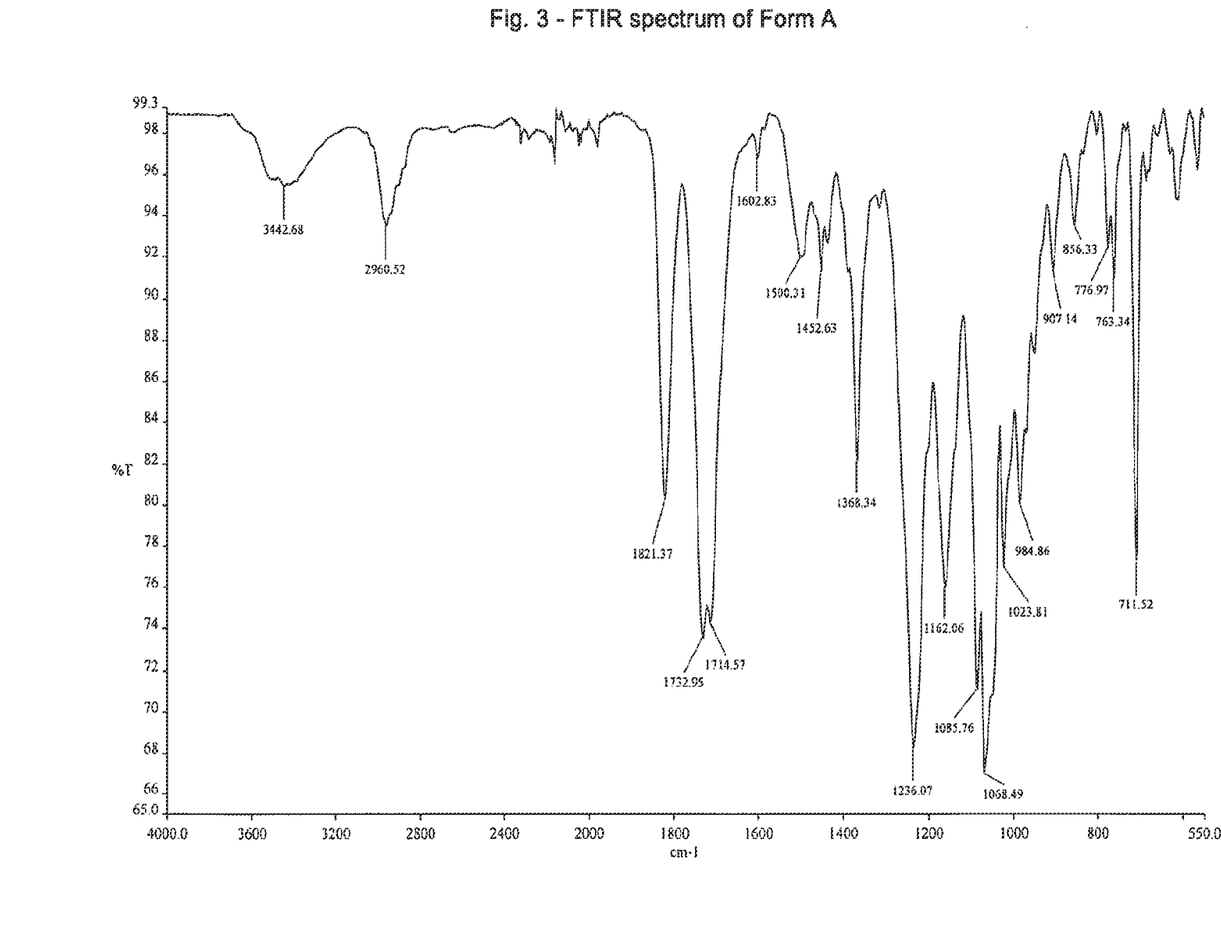

The IR spectrum of Form A (FIG. 3) shows the characteristic absorption frequencies at 3442; 2960, 1821, 1732, 1714, •1368, 1236, 1162, 1085, 1068, 984, 907, 776, 763, 711 $cm^{-1}$.

Figure 4:
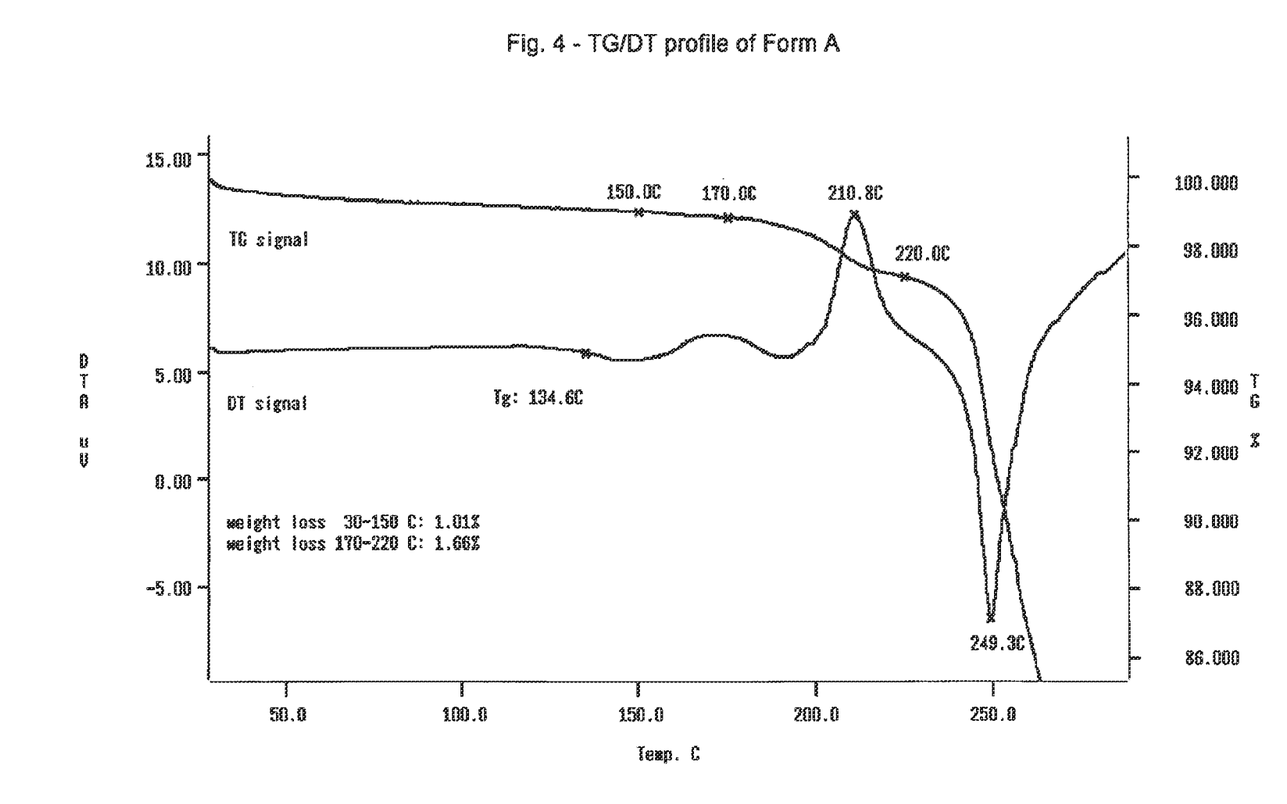

The TG/DT analysis of Form A (FIG. 4) confirms the DSC analysis showing a DT profile characterized by a baseline deflection due to $T_g$ between 130° C. and 143° C., an exothermic peak with maximum at about 211° C. due to recrystallisation of the melted product and the consequent melting peak with maximum at about 249° C. followed by decomposition. The TG profile shows a weight loss of about 1.0% from 30 to 150° C. due to release of residual moisture and a weight loss of about 1.6% which takes place upon recrystallisation followed by a massive weight loss due to a degradative reaction.

The optical microscopy shows that solid Form A is constituted by a glassy irregular particulate with a large variety of dimensions and absence of well-shaped crystal Forms.

Form B

Figure 5:
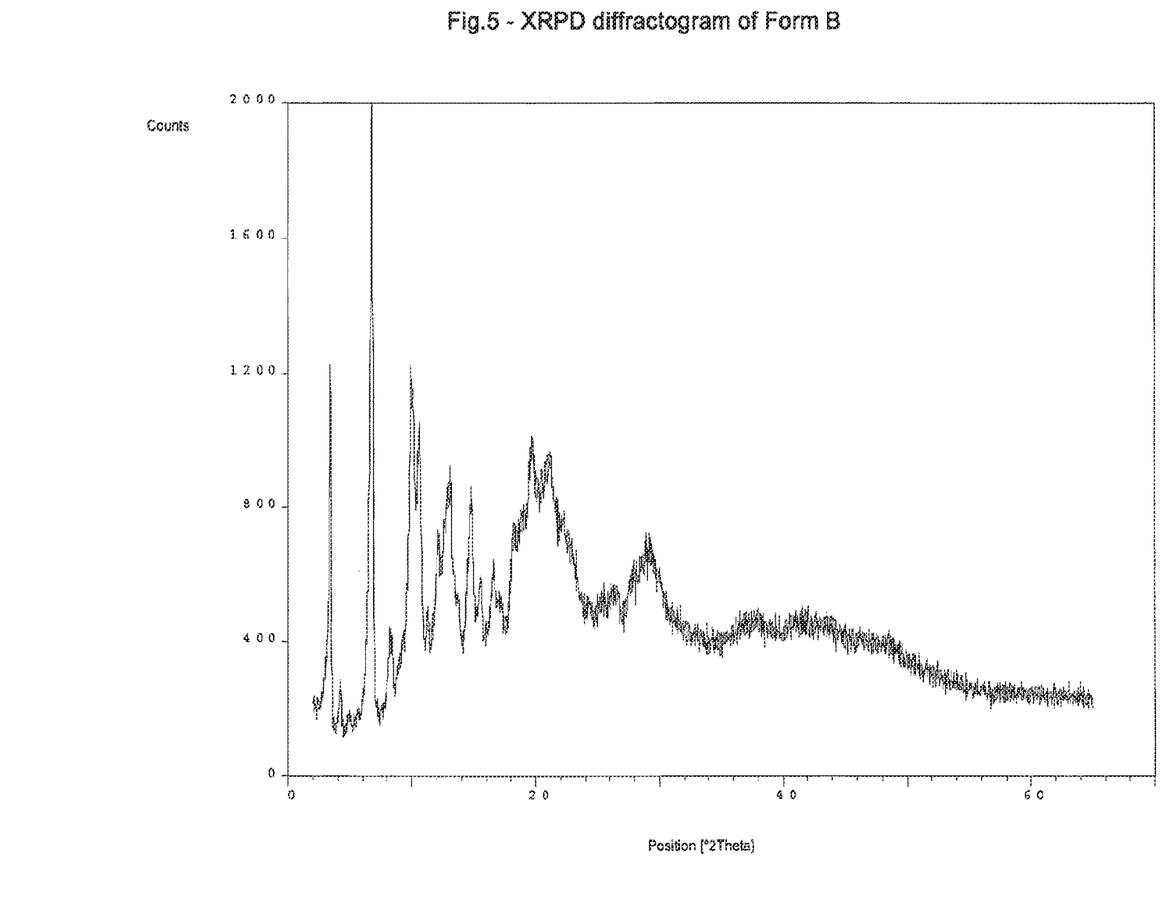
FIGS. 5-8: XRPD, DSC, TG/DTA and IR spectra of Form B.

The x-ray powder diffraction pattern of Form B (FIG. 5) shows a crystalline structure with useful distinctive peaks at approximately 3.5, 6.8, 9.9, 10.1, 10.7, 12.1, 13.1, 14.8, 18.2, 19.7, 21.3, 29.3 deg 2-theta.

Figure 6:
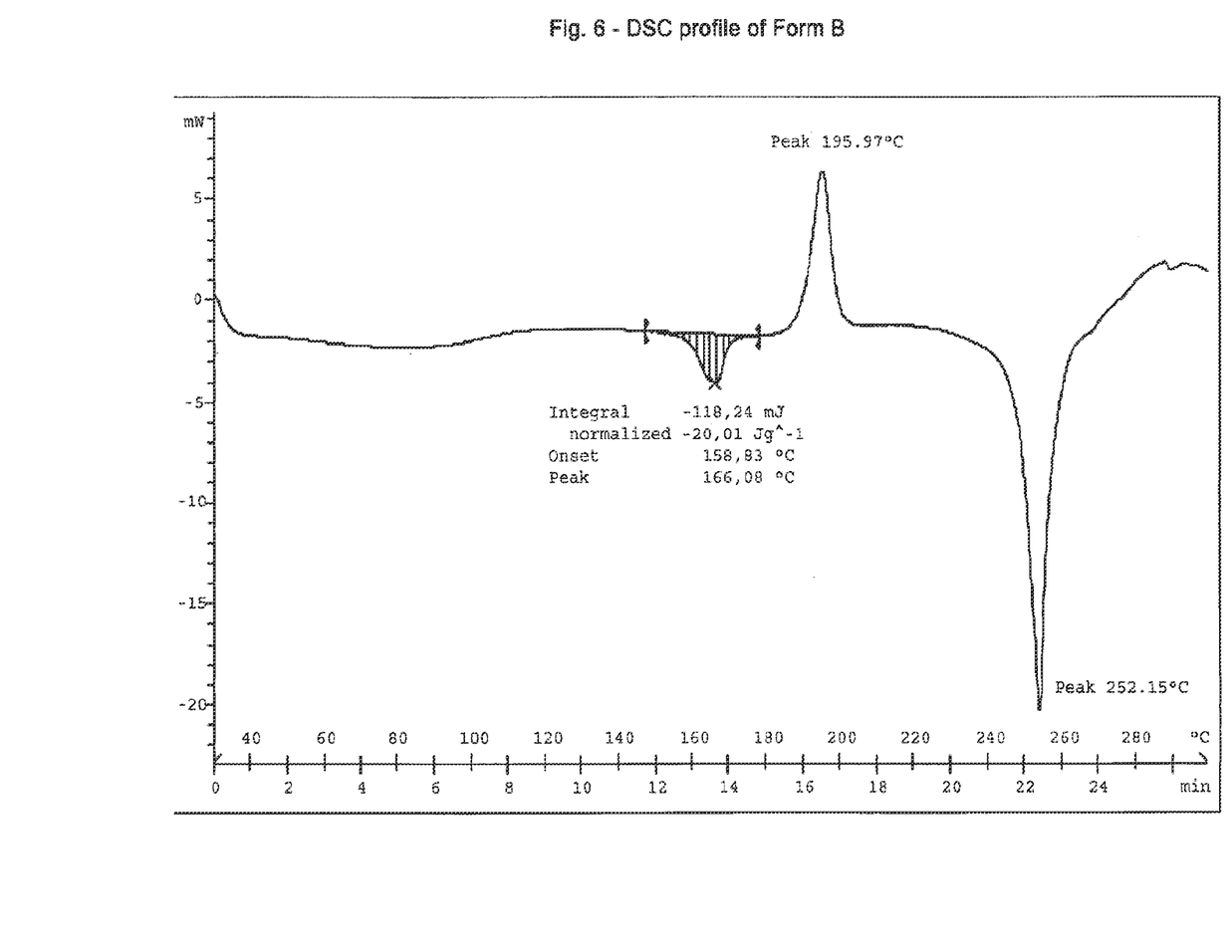

The DSC curve of Form B (FIG. 6) shows a weak and broad endothermic signal with maximum below 1 00° C., a first melting peak with maximum at about—166° C. and $\Delta H_{fus}$ of about—20 J/g, an exothermic peak with maximum at about 196° C. due to recrystallisation of the melted product and a second melting peak with maximum at about 252° C. followed by decomposition.

Figure 7:
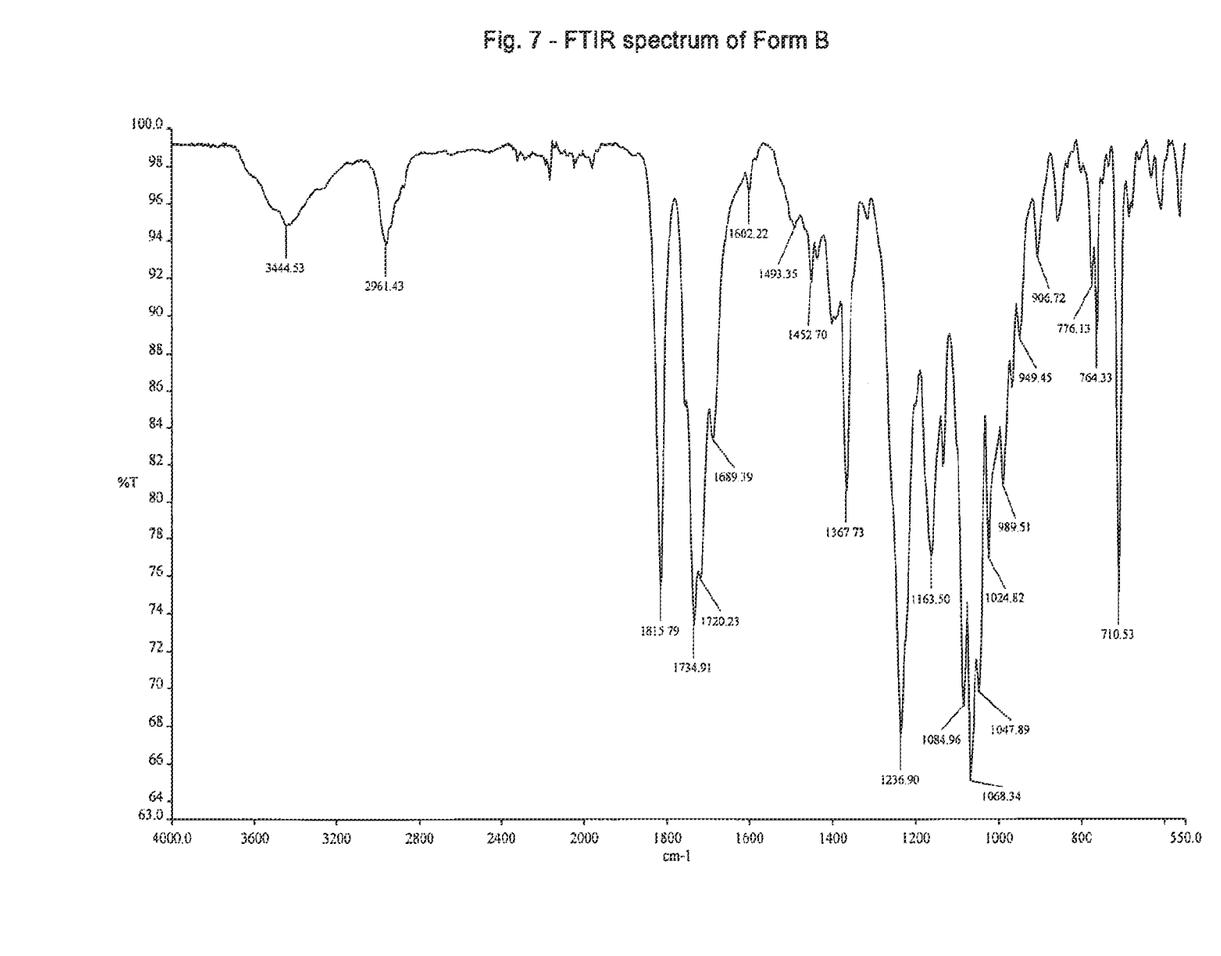

The IR spectrum of Form B (FIG. 7 shows the characteristic absorption frequencies at 3444, 2961, 1816, 1735, 1720, 1689, 1368, 1237, 1163, 1085, 1068, 1047, 989, 949, 907, 776, 764, 710 $cm^{-1}$.

Figure 8:
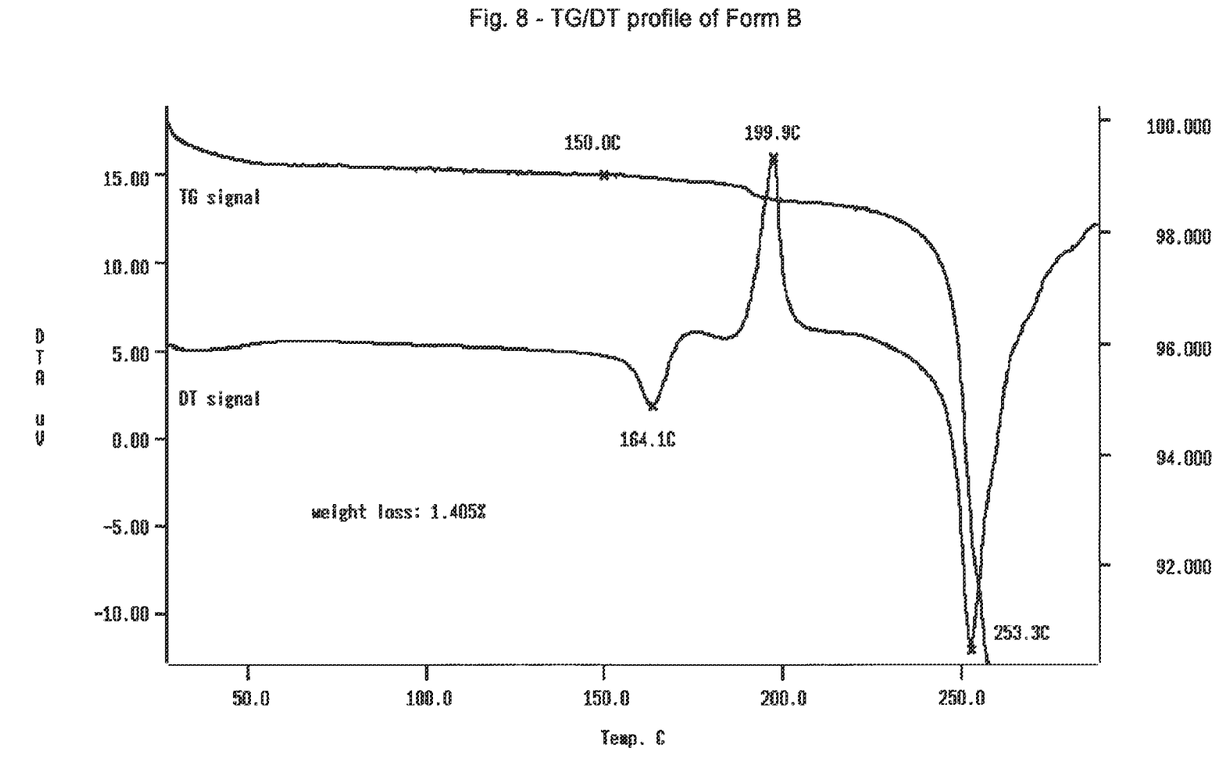

The TG/DT analysis of Form B (FIG. 8) confirms the DSC analysis showing a weak and broad endothermic signal with maximum below 100° C. due to release of residual moisture, a first melting peak with maximum at about 164° C., an exothermic peak with maximum at about 200° C. due to recrystallisation of the melted product and a second melting peak with maximum at about 253° C. followed by decomposition. In the TG profile, a weight loss of about 1.4% from 30 to 150° C. due to release of residual moisture is followed by a massive weight loss which takes place above 240° C. due to a degradative reaction.

The optical microscopy shows that solid Form B is constituted by acicular (needle-like) crystals.

Mixture of Form A and Form B

Figure 9:
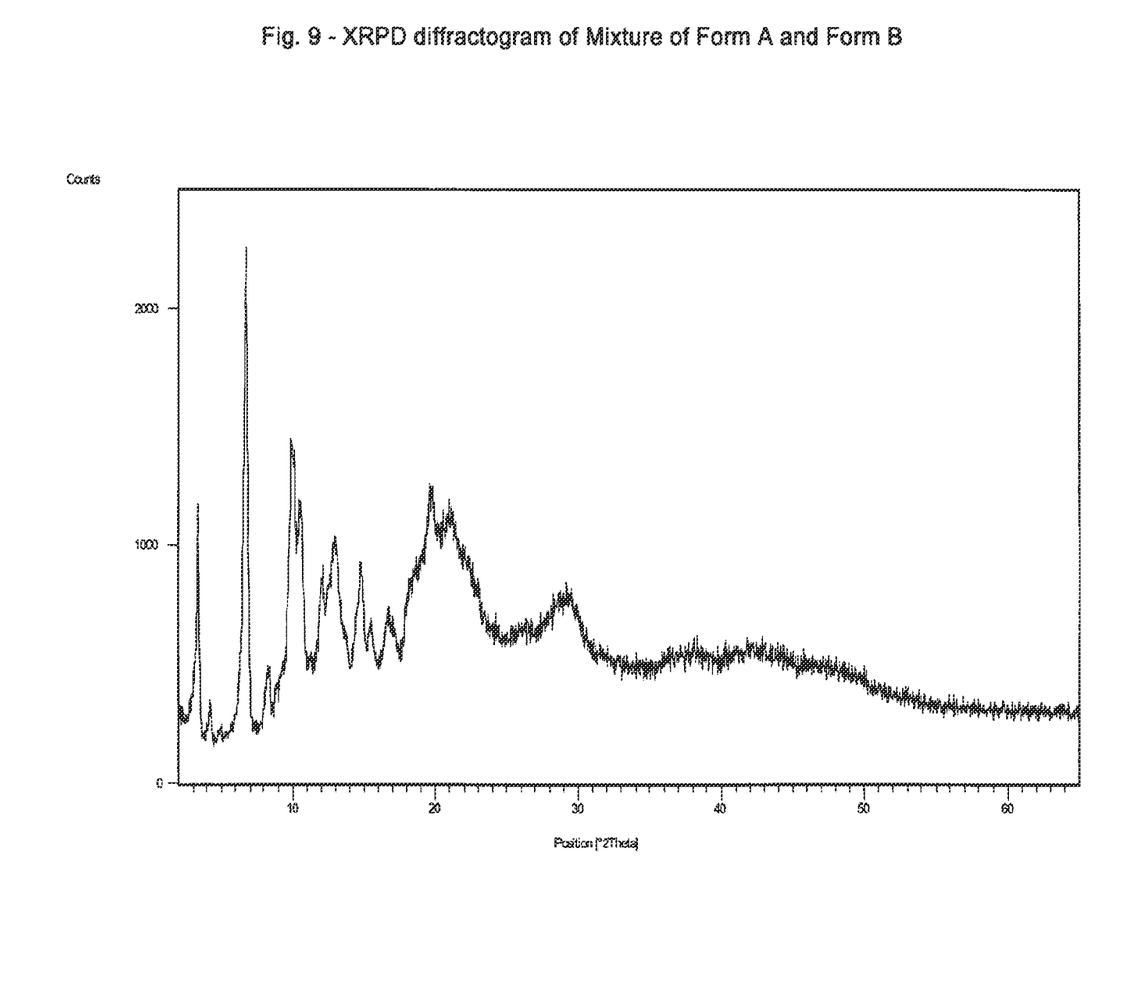
FIGS. 9-12: XRPD, DSC, TG/DTA and IR spectra of a mixture of Form A and Form B, containing about 75% of Form B.

The x-ray powder diffraction pattern of the mixture of Form A and Form B. (FIG. 9) shows a crystalline structure with distinctive peaks at approximately 3.4, 6.8, 9.9, 10.6, 12.1, 13.1, 14.8, 18.1, 19.7, 21.2 deg 2-theta due to the fraction of Form B in the mixture.

Figure 10:
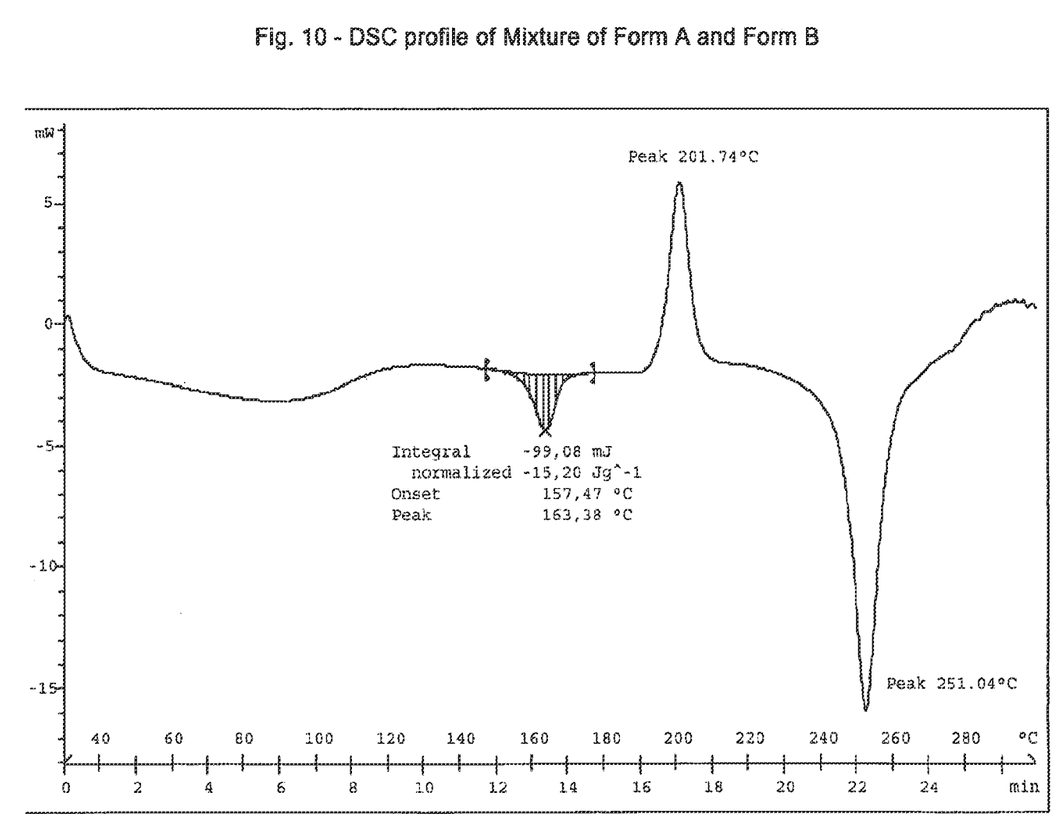

The DSC curve (FIG. 10) shows a weak and broad endothermic signal with maximum below 100° C., a first melting peak with maximum at about 163° C. and $\Delta H_{fus}$ of about –15 J/g, an exothermic peak with maximum at about 202° C. due to recrystallisation of the melted product and a second melting peak with maximum at about 251° C. followed by decomposition.

Figure 11:
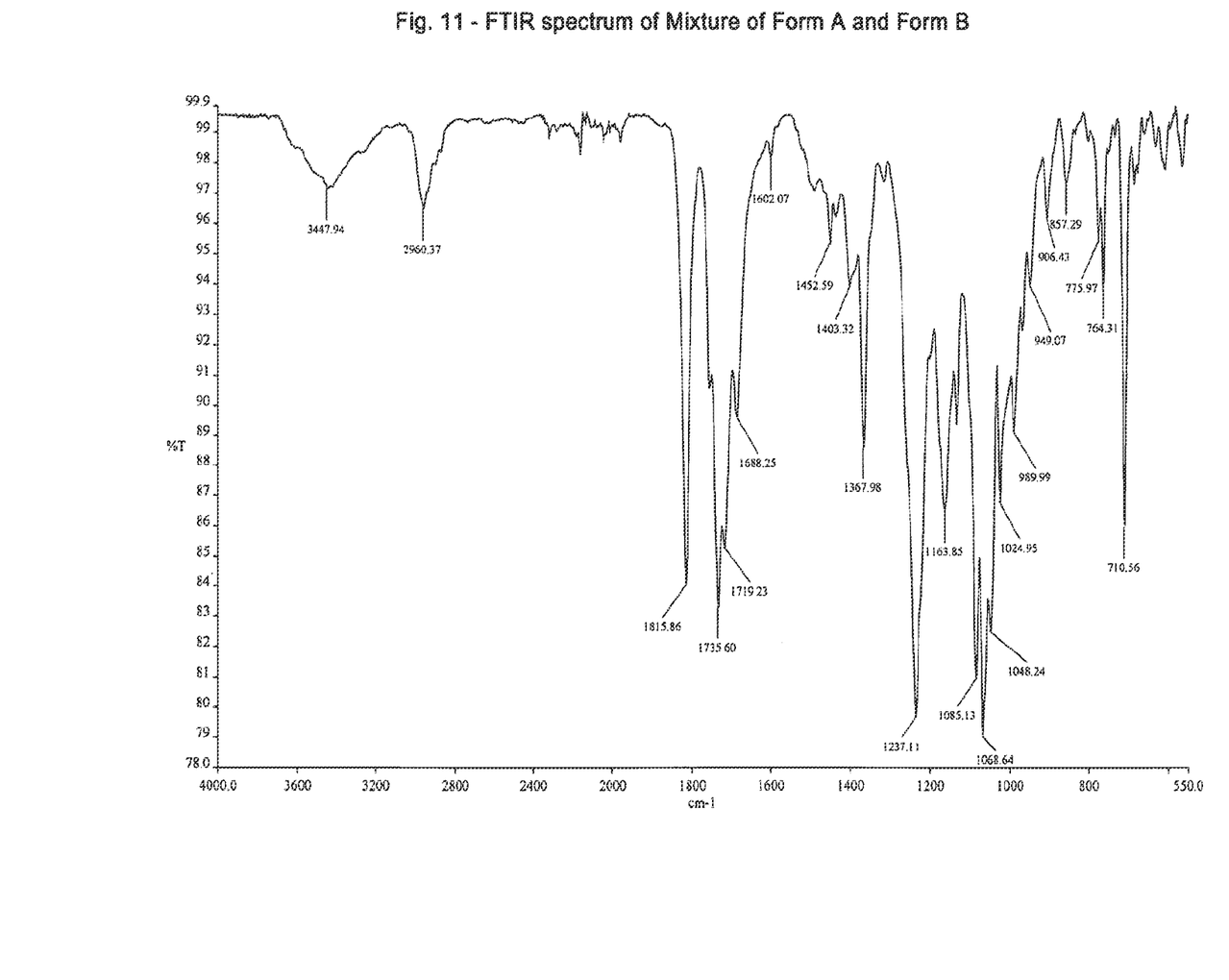

The IR spectrum (FIG. 11) shows characteristic absorption frequencies at 3448, 2960, 1816, 1735, 1719, 1688, 1368, 1237, 1164, 1085, 1068, 1048, 989, 949, 906, 776, 764, 710 $cm^{-1}$.

Figure 12:
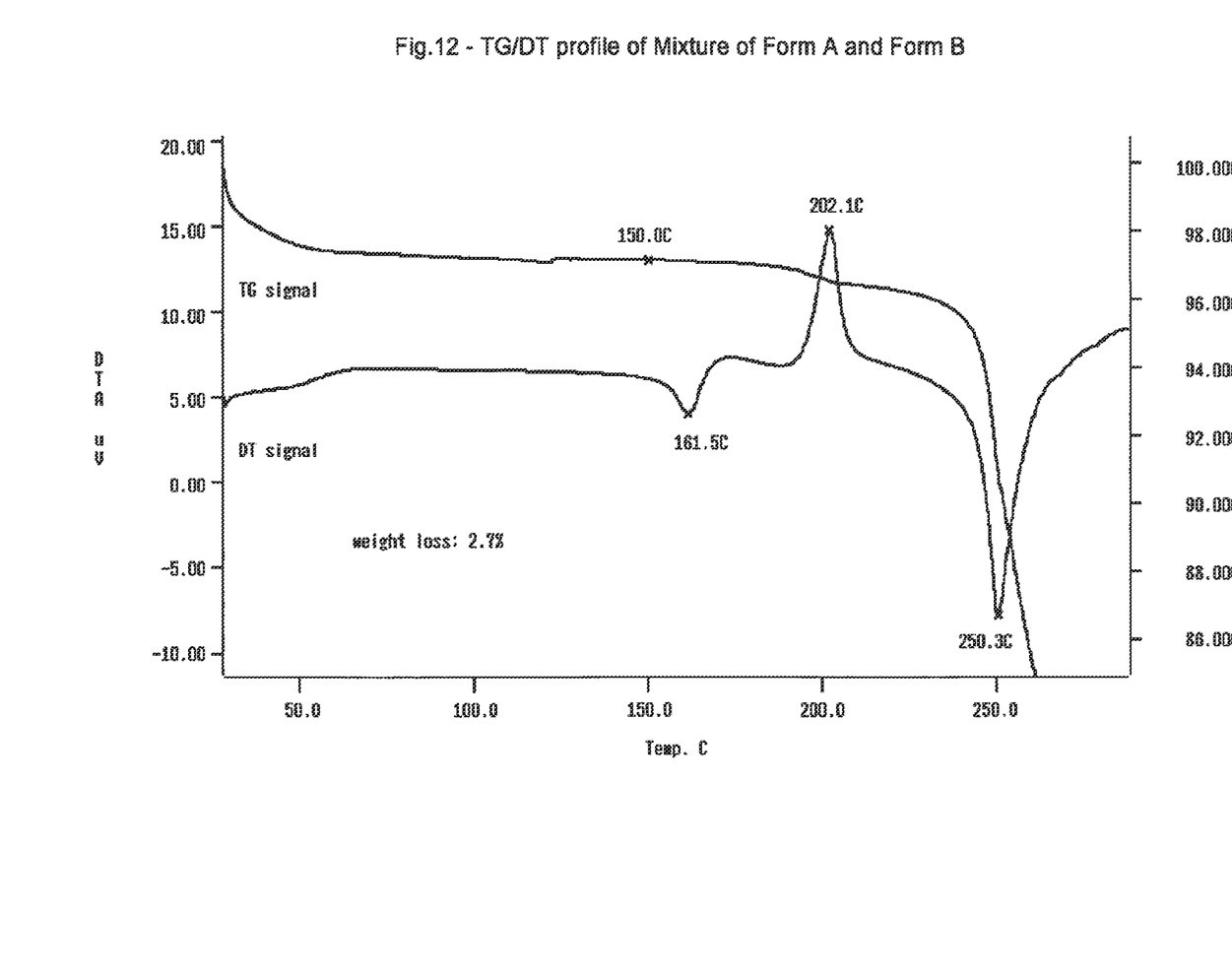

The TG/DT analysis (FIG. 12) confirms the DSC analysis showing a weak and broad endothermic signal with maximum below 100° C. due to release of residual moisture, a first melting peak with maximum at about 162° C., an exothermic peak with maximum at about 202° C. due to recrystallisation of the melted product and a second melting peak with maximum at about 250° C., followed by decomposition. In the TG profile, a weight loss of about 2.7% from 30 to 150° C. due to release of residual moisture is followed by a massive weight loss which takes place at 240° C. due to a degradative reaction.

Optical microscopy shows that the Mixture of Form A and Form B is constituted by prismatic crystals.

These data clearly indicate that polymorphic Forms A and B of Ortataxel are easy distinguishable from the pseudopolymorphic acetone solvate by means of XRPD, DSC, IR and analyses for the solvent content (such as thermogravimetry or gas-chromatography).

Materials and Methods

X-Ray Powder Diffraction Pattern (xrpd)

X-ray powder diffraction patterns were collected on a Philips PW1800 diffractometer. The x-ray generator was operated at 45 kV and 40 mA, using the Cu Kα line as radiation source. The sample was packed on a suitable slit and the irradiated length was 10 mm. The data were collected between 2 and 65 deg 2-theta with a step size of 0.02 deg 2-theta.

Differential Scanning Calorimetry (DSC)

Measurements of differential scanning calorimetry were performed using a Mettler TC15 System equipped with a DSC20 measuring cell, using closed aluminum crucibles (40 μl volume) with a pinhole. Heat flow was recorded from 30 to 300° C. with a linear heating rate of 10° C./min under a 50 ml/min nitrogen flow. About 5 mg of powder was used for each measurement.

Thermogravimetry and Differential Thermal Analysis (TG/DTA)

The analyses were performed using a Seiko TG/DTA6200 simultaneous system using open aluminum pans (40 μl volume). The TG/DT signals were recorded from 30 to 300° C. with linear heating rate (10° C./min) under a 200 ml/min nitrogen flow. About 10 mg of powder was used for each measurement.

Fourier Transform Infrared Spectroscopy (FTIR)

The infrared spectra were recorded with ATR technique using a Fourier-transform spectrometer Perkin Elmer Spectrum One. The spectra were the result of the acquisition and transformation of 16 co-added scans in the 4000-550 $cm^{-1}$ spectral region at a resolution of 4 $cm^{-1}$.

Optical Microscopy

The analyses were performed using a transmitted-light microscope Zeiss Axioskop. For each analysis a little amount of sample was dispersed in silicone oil, mounted on a specimen slide and covered with a micro cover glass. The observations were carried out under appropriate conditions of illumination, contrast and magnification.

EXAMPLE 1

Preparation of Form A

Ortataxel (13 g) was dissolved in acetone (112.5 mL). Purified water (555 mL) containing citric acid (12 mg) was rapidly added under stirring, causing the precipitation of an amorphous solid which was filtered and washed with water (65 mL) containing citric acid (18 mg). The sample was dried at 40° C. for 48 hours affording 12 g of a white solid having the characteristic XRPD, DSC, IR and TG/DTA reported in FIGS. 1-4 respectively.

EXAMPLE 2

Preparation of Form B

Ortataxel (14 g) was dissolved in 95% ethanol (168 mL) containing citric acid (28 mg) at 50° C. Cold demineralised water (280 mL) was added to the resulting solution over 15 minutes. The suspension was stirred at 40° C. for 6 hours. The mixture was cooled down to 20° C. and the white solid was filtered off. The solid was washed with a solution of ethanol (168 mL) and water (280 mL). The solid was dried under vacuum at 50° C. for 40 hours affording 13.4 g of a white solid having the characteristic XRPD, DSC, IR and TG/DTA reported in FIGS. 5-8 respectively.

EXAMPLE 3

Preparation of a Mixture of about 25% Form A and 75% Form B

Ortataxel (14 g) was dissolved in 95% ethanol (168 mL) containing citric acid (28 mg) at 50° C. Cold demineralised water (280 mL) was added to the resulting solution over 15 minutes. The mixture was promptly cooled down to 20° C. and the white solid was filtered off. The solid was washed with a solution of ethanol (168 ml) and water (280 mL) containing citric acid (25 mg). The solid was dried under vacuum at 50° C. for 40 hours affording 13.4 g of white material having the characteristic XRPD, DSC, IR and TG/DTA reported in FIGS. 9-12 respectively.

EXAMPLE 4

Preparation of Mixtures of Form A and Form B in Various Proportions

Figure 13:
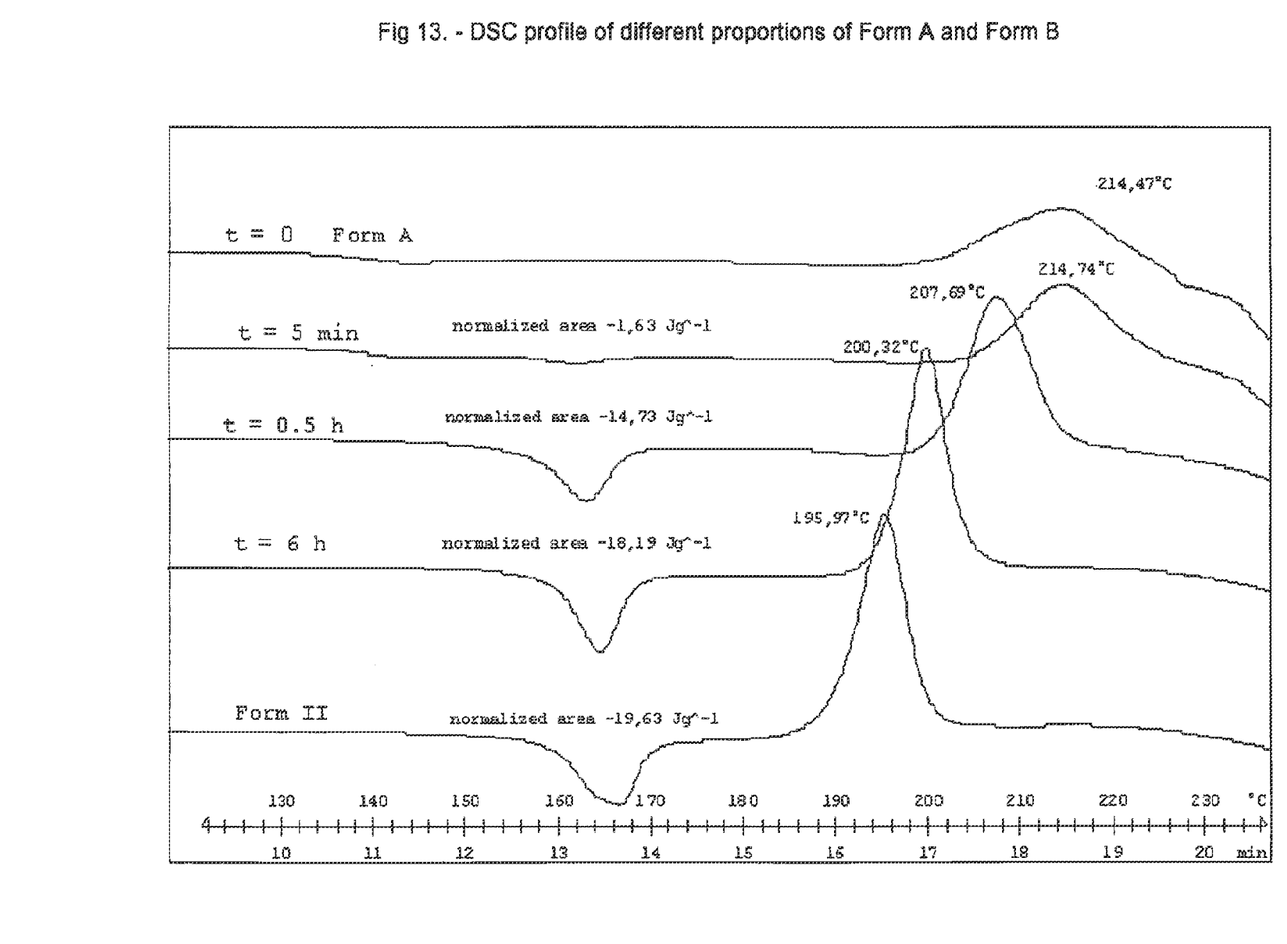
FIG. 13: DSC profile of different proportions of Form A and Form B.

Form A (1 g) was suspended in a mixture of 95% ethanol (12 ml) and water (20 ml) containing citric acid (2 mg) at 40° C. Samples were taken at different times (t=0, t=5 min, t=30 min, t=6 h) in order to demonstrate that different proportions of Form A and Form B can be obtained. FIG. 13 shows 20 the DSC analysis of the samples compared to the curve of pure Form B.

The invention claimed is:

1. A process for preparing an amorphous solid Ortataxel, the process comprising the steps of dissolving Ortataxel in a ketone, an aprotic dipolar organic solvent, or mixtures thereof, followed by adding water containing 0.001% w/v to 0.003% w/v of an organic acid, thereby producing an amorphous solid Ortataxel.

2. An amorphous solid Ortataxel [13-(N-Boc-p-isobutylserinyl)-14-β-hydroxybaccatin III 1,14-carbonate] made by the process of claim 1.

3. The process according to claim 1, wherein the aprotic dipolar organic solvent is acetone, dimethylsulfoxide, or mixtures thereof.

4. The process according to claim 3, wherein the organic acid is citric acid or ascorbic acid.

5. The process according to claim 3, wherein the organic acid is citric acid.

6. A process for preparing a crystalline solid Ortataxel, the process comprising the step of dissolving an Ortataxel in a protic organic solvent containing 0.01% w/v to 0.03% w/v of an organic acid, followed by adding water and stirring at a temperature ranging from 0° C. to 60° C. for a time ranging from 4 hours to 8 hours.

7. A crystalline solid Ortataxel [13-(N-Boc-β-isobutylserinyl)-14-β-hydroxybaccatin III 1,14-carbonate], wherein the crystalline solid Ortataxel is in a non-solvate form and has a X-ray powder diffraction pattern including peaks of, 6.8 °2θ, 12.1 °2θ, or 13.1 °2θ.

8. The process of claim 6, wherein the Ortataxel dissolved is an Ortataxel acetone solvate or an amorphous solid Ortataxel.

9. The process according to claim 6, wherein the temperature is 40° C.

10. The process according to claim 9, wherein the stirring step is carried out for 6 hours.

11. The process according to claim 10, wherein the organic acid is acetic acid, ascorbic acid or citric acid.

12. A mixed solid Ortataxel, the mixed solid Ortataxel being in a non-solvate form and comprising the amorphous solid Ortataxel [13-(N-Boc-β-isobutylserinyl)-14-β-hydroxybaccatin III 1,14-carbonate] and the crystalline solid Ortataxel of claim 7.

13. The mixture according to claim 12, wherein the amount of the crystalline solid Ortataxel is about 75% by weight.

14. A process for preparing a mixed solid Ortataxel, the process comprising the steps of suspending an Ortataxel in a mixture of a protic organic solvent and water containing an organic acid and stirring for less than 4 hours and at a temperature ranging from 0° C. to 60° C., wherein the process produces a mixed solid Ortataxel comprising the amorphous solid Ortataxel [13-(N-Boc-β-isobutylserinyl)-14-β-hydroxybaccatin III 1,14-carbonate] and the crystalline solid Ortataxel of claim 7.

15. The process according to claim 14, wherein the Ortataxel suspended is Ortataxel acetone solvate or an amorphous Ortataxel.

16. The process according to claim 15, wherein the protic organic solvent ratio to water ranges from 0.5 to 0.7.

17. The process according to claim 16, wherein the temperature is 40° C.

18. The process according to claim 15, wherein the organic acid is citric acid or ascorbic acid.

19. The process according to claim 18, wherein the organic acid is citric acid.

20. A pharmaceutical composition comprising an Ortataxel in admixture with suitable excipients and/or carriers, wherein the Ortataxel is the amorphous solid Ortataxel [13-(N-Boc-β-isobutylserinyl)-14-β-hydroxybaccatin III 1,14-carbonate], the crystalline solid Ortataxel of claim 7, or mixtures thereof.

21. A method for treating cancer comprising administering to a patient in need thereof a composition comprising the pharmaceutical composition of claim 20.

22. The process according to claim 11, wherein the organic acid is citric acid.

23. The process according to claim 6, wherein the protic organic solvent is methanol, ethanol or isopropanol.

24. The process according to claim 6, wherein the protic organic solvent is ethanol.

25. The process according to claim 14, wherein the organic acid is in an amount of 0.01%-0.03% w/v.

26. The process according to claim 14, wherein the protic organic solvent is methanol, ethanol or isopropanol.

27. The process according to claim 14, wherein the protic organic solvent is ethanol.

* * * * *